United States Patent [19]

Horodysky et al.

[11] Patent Number: 4,992,184

[45] Date of Patent: * Feb. 12, 1991

[54] PHOSPHITE SULFONATE REACTION PRODUCTS AS MULTIFUNCTIONAL ADDITIVES

[75] Inventors: Andrew G. Horodysky, Cherry Hill, N.J.; Derek A. Law, Yardley; Shi-Ming Wu, Newtown, both of Pa.

[73] Assignee: Mobil Oil Corporation, Fairfax, Va.

[*] Notice: The portion of the term of this patent subsequent to Jan. 30, 2007 has been disclaimed.

[21] Appl. No.: 381,891

[22] Filed: Jul. 19, 1989

[51] Int. Cl.$^5$ ............... C10M 135/10; C10M 137/04
[52] U.S. Cl. .................... 252/32.7 E; 252/32.7 R; 252/46.6; 252/46.7; 252/389.21; 252/389.22; 252/400.21; 252/400.22; 558/86; 558/218
[58] Field of Search ............... 252/32.5, 32.7 R, 33, 252/32.7 E

[56] References Cited

U.S. PATENT DOCUMENTS

| | | | |
|---|---|---|---|
| 4,532,057 | 7/1985 | Horodysky | 252/49.8 |
| 4,557,845 | 12/1985 | Horodysky | 252/32.5 |
| 4,704,218 | 11/1987 | Horodysky | 252/46.6 |
| 4,897,269 | 1/1996 | Law | 252/32.5 |

*Primary Examiner*—Olik Chaudhuri
*Assistant Examiner*—Ellen McAvoy
*Attorney, Agent, or Firm*—A. J. McKillop; C. J. Speciale; H. M. Flournoy

[57] ABSTRACT

Phosphites of hydrocarbyl diols or alkoxylated amines are reacted with aryl sulfonic acids preformed or formed in situ in lubricants to provide multifunctional antioxidant, corrosion inhibiting, and friction reducing properties therefor.

42 Claims, No Drawings

PHOSPHITE SULFONATE REACTION PRODUCTS AS MULTIFUNCTIONAL ADDITIVES

BACKGROUND OF THE INVENTION

This application is directed to the use of additive concentrations of neutralized metallic hydrocarbyl sulfonate/dialkyl cyclic (or non-cyclic) phosphite reaction products in premium quality industrial, automotive and marine lubricants which provide a "time-release" dosage of multifunctional friction reducing antiwear properties and thus extend service life.

Lubricants, such as lubricating oils and greases, are subject to oxidative deterioration at elevated temperatures or upon prolonged exposure to the elements. Such deterioration is evidenced, in many instances, by an increase in acidity and in viscosity, and when the deterioration is severe enough, it can cause metal parts to corrode. Additionally, severe oxidation leads to a loss of lubrication properties, and in especially severe cases this may cause complete breakdown of the device being lubricated. Many additives have been tried. However, many of them are only marginally effective except at high concentrations. Improved antioxidants are clearly needed.

Antioxidants or oxidation inhibitors are used to minimize the effects of oil deterioration that occur when hot oil is contacted with air. The degree and rate or oxidation will depend on temperature, air and oil flow rates and, of particular importance, on the presence of metals that may catalytically promote oxidation. Antioxidants generally function by prevention of chain peroxide reaction and/or metal catalyst deactivation. They prevent the formation of acid sludges, darkening of the oil and increases in viscosity due to the formation of polymeric materials.

Water (moisture) is another critical problem. In spite of even extraordinary precautionary efforts water is found as a film or in minute droplets in vessels containing various hydrocarbon distillates. This brings about ideal conditions for corrosion and damage of metal surfaces of the vessels and the materials contained therein. Also in the lubrication of internal combustion engines, for example, quantities of water are often present as a separate phase within the lubricating system. Another serious problem in respect to metallic surfaces in contact with adjacent metallic surfaces is the surface wear caused by the contact of such surfaces. One material capable of simultaneously effectively coping with such problems as these is highly desirable.

Lubricants in service applications often generate acid species or acid-forming species, especially when exposed to high operating temperatures, extended service life and/or contact with atmospheric oxygen during aeration caused by churning or moving elements of the lubricated machine. Acid-forming species can also be formed via hydrolysis or other similar mechanisms.

Metallic aryl sulfonates such as calcium dinonylnaphthalene sulfonates have been widely used in petroleum and synthetic lubricants as rust and corrosion inhibiting additives. Additionally, these and related metallic aryl sulfonates have, on occasion, provided good detergency and demulsibility properties in a variety of lubricant formulations.

It has now been found that if metallic aryl sulfonates are used as additives in systems as described above, neutralization or acidification to form sulfonic acids can occur. If both metallic aryl sulfonates and di- or trialkyl diol or alkoxylated amine phosphites are used together in a lubricant, or alternatively pre-reacted, these sulfonic acids and phosphites can react to form sulfonate esters and lower phosphites having one less alkyl substitutent group. This mechanism can thus provide a "time-release" dosage of friction reducing, corrosion inhibiting or antiwear additives during the latter stages of lubricant service life when performance improvement is most needed. This phenomena can also be effectively used to neutralize potentially harmful acid substances as soon as they are generated. These remarkable benefits can be provided for a variety of synthetic and mineral oil based lubricants.

It is an object of this invention to provide both (a) a unique lubricant additive composition made by the reaction of at least partially neutralized or acidified sulfonates with alkanediol or alkoxylated amine phosphites, and (b) a method of providing for "time release" friction reducing, corrosion inhibiting, and/or antiwear properties via appropriate blending of sulfonate and phosphite components, allowing for the acidification or neutralization of the sulfonate in situ, in service and then the co-reaction of the acidified sulfonate and diol or alkoxylated amine phosphite while in use.

To the best of our knowledge the compositions in accordance with the invention have not been previously used as multifunctional additives in lubricating oils or greases or other solids lubricants. The use of reaction products of acidified sulfonates and cyclic phosphites or alkoxylated amine phosphites as multifunctional additives has not been reported in the literature and are believed to be novel. The composition of matter, the lubricant compositions containing such additives, and the use of such reaction products and lubricants to improve the performance properties are also unique.

The use of sulfonates and diol-derived or alkoxylated amine phosphites as "time-release" multifunctional additives for lubricants which function via at least partial neutralization or acidification followed by phosphite esterification is also believed to be both unique and novel.

SUMMARY OF THE INVENTION

In accordance with the invention there is provided by the use of additive concentrations of at least partially neutralized or acidified metallic hydrocarbyl sulfonate/hydrocarbyl (dialkyl) cyclic phosphite reaction products in premium quality industrial, automotive and marine lubricants, superior lubricating fluids which provide a "time-release" dosage of multifunctional friction reducing antiwear properties and thus extend service life. Hydrocarbyl as used herein includes but is not limited to alkyl, alkenyl, aryl, alkenyl, alkaryl, aralkyl, and cycloalky, and/or mixtures thereof. The unique compositions described in this patent application are readily prepared in a one-pot process in existing equipment using known technology. With these "time-release" EP/antiwear, friction reducing additives providing in-situ reaction by appropriate blending of sulfonate/phosphite (cyclic or non-cyclic) additive components extended service life premium lubricants are provided.

DESCRIPTION OF SPECIFIC EMBODIMENTS

Metallic hydrocarbyl aryl sulfonates can be neutralized or acidified in service, in situ, or via addition of small quantities of organic or inorganic acids, as shown below:

$$(ArSO_3)_nM + nH^+ \rightarrow nArSO_3H + M^{n+}$$

where n is an integer equal to the valence number of M, Ar is a $C_{12}$ to about $C_{32}$ dialkylnaphthalene, or dihydrocarbylarene, or any alkyl aromatic, and M is alkali metal, or alkaline-earth metal and/or a nitrogenous group such as amine or ammonium. The above acid can then react in service or in situ with any phosphite, preferably cyclic or amine-containing phosphite to form multifunctional additives with enhanced antiwear, friction reducing and/or corrosion inhibiting properties. The non-traditional phosphites include cyclic phosphites of long-chain or short-chain diols, and phosphites of alkoxylated hydrocarbyl amines including phosphites of bis(2-hydroxyethyl)oleylamine, polyethoxylated tallowamine, 2-hydroxypropylcocoamine, and the like. The phosphites are made by reaction of a dihydrocarbyl phosphite with the appropriate hydroxyl group containing moiety such as diol or alkoxylated amine.

The alkoxylated amine and amine-phosphites are as generally described in U.S. Pat. No. 4,557,845 which is incorporated herein in its entirety by reference thereto. The amines useful herein can also be alkoxylated hydrocarbyl diamines, or alkoxylated etheramines. Usually the amine-phosphites are prepared by reacting an alkoxylated hydrocarbyl amines of the following generalized formula:

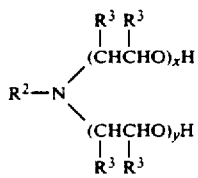

wherein $R^2$ is a $C_6$ to about $C_{30}$ hydrocarbyl group or sulfur, nitrogen and/or oxygen-containing hydrocarbyl group, $R^3$ is hydrogen or a $C_1$ to $C_6$ hydrocarbyl group, and x and y are intergers of from 0 to 50, at least one of which is not 0, with a phosphite of the following generalized formula:

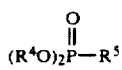

wherein $R^4$ is a $C_1$ to $C_6$ hydrocarbyl group and $R^5$ is hydrogen or a $C_1$ to $C_6$ hydrocarbyl group preferably hydrocarbyl is alkyl or mixtures thereof.

Preferred alkoxylated amines include but are not limited to the group consisting of 2-hydroxyethylhexylamine, 2-hydroxyethyloctylamine, 2-hydroxyethyldodecyclamine, 2-hydroxyethyltetradecylamine, 2-hydroxyethyleicosylamine, 2-hydroxyethyltriacontylamine, 2-hydroxyethyloleylamine, 2-hydroxyethyltallowamine, 2-hydroxyethylsoyamine, bis(2-hydroxyethyl)hexylamine, bis(2-hydroxyethyl)octylamine, bis(2-hydroxyethyl)dodecylamine, bis(2-hydroxyethyl) tetradecylamine, bis(2-hydroxyethyl)pentadecylamine, bis(2-hydroxyethyl)eicosylamine, bis(2-hydroxyethyl)triacontylamine, bis(2-hydroxyethyl)oleylamine, bis(2-hydroxyethyl)tallowamine, bis(2-hydroxyethyl) soyamine, 2-hydroxypropylhexylamine, 2-hydroxypropyloctylamine, 2-hydroxypropdodecylamine, 2-hydroxypropyltetradecylamine, 2-hydroxypropylpentadecylamine, 2-hydroxypropyleicosylamine, 2-hydroxypropyltriacontylamine, 2-hydroxypropyloleylamine, 2-hydroxypropyltallowamine, 2-hydroxypropylsoyamine, bis(2-hydroxypropyl)hexylamine, bis(2-hydroxypropyl)octylamine, bis(2-hydroxypropyl)dodecylamine, bis(2-hydroxypropyl)tetradecylamine, bis(2-hydroxypropyl)pentadecylamine, bis(2-hydroxypropyl)eicosylamine, bis(2-hydroxypropyl)triacontylamine, bis(2-hydroxypropyl)oleylamine, bis(2-hydroxypropyl)soyamine or mixtures thereof.

The hydrocarbyl or dihydrocarbyl diol derived phosphites are as generally described in U.S. Pat. No. 4,704,218 which is incorporated herein in its entirety by reference thereto and have the generalized formula:

$$R^1(OH)_2$$

wherein $R^1$ is a hydrocarbyl group having from 10 to about 30 carbon atoms, $R^1$ can also optionally contain N, S, and/or O.

Included are phosphites derived from diol esters such as glycerol monooleate, glycerol monohexanoate or any glycerol monoester; trimethylolpropane monooleate, trimethylolpropane monostearate, trimethylolpropane monohexanate or similar monoesters; pentaerythritol didecanoate, pentaerythritol diisostearate or similar diesters. Although cyclic phosphites are preferred non-cyclic or oligomeric phosphites can also be used. The phosphites are as described in either U.S. Pat. Nos. 4,557,845 or 4,704,218 and have the generalized formula:

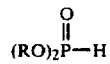

wherein said R is a $C_1$ to a $C_6$ hydrocarbyl group preferably alkyl or mixtures thereof and hence preferably selected from methyl, ethyl, propyl, butyl, pentyl, hexyl or mixtures thereof.

Preferred diols include but are not limited to the group consisting of 1,2-decanediol, 1,2-dodecanediol, 1,2-tetradecanediol, 1,2-pentadecanediol, 1,2-hexadecanediol, 1,2-heptadecanediol, 1,2-octadecanediol and mixtures thereof and as noted hereinabove diol esters.

The reactants are preferably used in equimolar quantities although less than molar or more than molar quantities may be used. The invention therefore contemplates products made by using molar ratios of sulfonate to amine-phosphite or diol-phosphite of 10:1 to about 1:10.

The temperature of reaction will depend upon the solvent used, since the reaction will generally be run at the temperature of reflux. The temperature is not believed to be critical and the reaction can be run over a wide range, from about 50° to about 225° C., preferably from about 80° to about 150° C.

Although a solvent is not required, examples of useful solvents include but are not limited to toluene, benzene, xylene, cyclohexane, ethanol and the like. Where a solvent is used, it should be one in which the products are soluble and which can be relatively easily removed, although in some cases a lubricating oil can be used as a solvent and/or diluent.

Times of reaction are not critical, but they will vary depending upon the size and complexity of the reactants. Under normal conditions, the reaction with the contemplated reactants can be completed in from about one hour to about ten hours or more preferably from about two hours to about six hours.

Other additives, such as detergents, dispersants, antioxidants, antiwear agents, extreme pressure additives, pour depressants, antirust additives and the like may be present in the compositions of the present invention. These can include phenates, sulfonates, polymeric succinimides, zinc dialkyl or aryl dithiophosphates, polymers, calcium and magnesium salts, polymeric viscosity index improving additives such as olefin copolymers, sulfurized olefins and the like.

The compounds of the invention are used with lubricating oils or greases to the extent of from about 0.01% to about 10% by weight of the total composition, preferably from about 0.2% to about 2%.

The lubricants contemplated for use with the novel additive products herein disclosed include mineral and synthetic hydrocarbon oils of lubricating viscosity, mixtures of mineral oils and synthetic oils and greases from any of these, including the mixtures. The synthetic hydrocarbon oils include long-chain alkanes such as cetanes and olefin polymers such as oligomers of hexene, octene, decene and dodecene, etc. Vicinal diol-derived phosphites are especially effective in synthetic oils formulated using mixtures of synthetic hydrocarbon olefin oligomers and lesser amounts of hydrocarbyl carboxylate ester fluids. The other synthetic oils, which can be used alone with the compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di-and tripentaerhthritol, with an aliphatic monocarboxylic acid containing from 1 to 20 carbon atoms, or mixtures of such acids.

A wide variety of thickening agents can be used in the greases of this invention. Included among the thickening agents are alkali and alkaline earth metal soaps of fatty acids and fatty minerals having from about 12 to about 30 carbon atoms per molecule. The metals are typified by sodium, lithium, calcium and barium. Fatty materials are illustrated by stearic acid, hydroxystearic acid, stearin, cottonseed oil acids, oleic acid, palmitic acid, myristic acid and hydrogenated fish oils.

Other thickening agents include salt and salt-soap complexes such as calcium stearate-acetate (U.S. Pat. No. 2,197,263), barium stearate acetate (U.S. Pat. No. 2,564,561), calcium stearate-caprylate-acetate complexes (U.S. Pat. No. 2,999,065), calcium caprylate-acetate (U.S. Pat. No. 2,999,066), and calcium salt and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline.

The preferred thickening/gelling agents employed in the grease compositions are essentially hydrophobic clays. Such thickening agents can be prepared from clays which are initially hydrophilic in character, but which have been converted into a hydrophobic condition by the introduction of long chain hydrocarbon radicals into the surface of the clay particles; prior to their use as a component of a grease composition, as, for example, by being subjected to a preliminary treatment with an organic cationic surface active agent, such as an onium compound. Typical onium compunds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further disucssion, and does not form a part of the present invention.

More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolie, biotite, vermiculite, zeolite clays, and the like.

The following examples typify but are not meant in any way to limit the invention.

CYCLIC PHOSPHITE-ARYL SULFONIC ACID REACTION PRODUCT

Example 1

A one liter, four-neck flask was equipped with thermometer, $N_2$ sparger, condenser, and agitator. Approximately 112 g mol of calcium dinonylnaphthalene sulfonate (commercially obtained from King Industries, Inc. as Nasul 729) in 100 ml of toluene was charged to the reactor and acidified with 4.9 ml of 30% sulfuric acid and reacted for one hour at 60° C. A mixed hexadecane- and octadecane-1,2-diol phosphite (38 g, 0.12 mol) was then added in one portion. This phosphite was prepared as generally described in U.S. Pat. No. 4,532,057 which is incorporated as a reference in its entirety. The mixture was heated to reflux for four hours, filtered and washed with toluene. The combined filtrate and washings were washed with water (2×50 ml), dried over $MgSO_4$ and evaporated under a reduced pressure at 110° C. yield 158 g of viscous brown fluid.

ALKOXYLATED AMINE-PHOSPHITE-ACIDIFIED Sulfonate Reaction Product

Example 2

To a stirred solution of bis(2-hydroxyethyl)oleylamine (35.2 g, 0.10 mol) in 100 ml of toluene was added tributyl phosphite (25 g, 0.10 mol) dropwise under $N_2$ atmosphere. The mixture was heated to 70° C. for two hours before 96 g of Nasul 729 was added. The mixture was stirred at 90° C. for one hour, then 4 ml of 30% sulfuric acid was charged to the reaction mixture, and was further heated to reflux for four hours. The final mixture was filtered, the filtrate was washed with water, dried, and evaporated under a reduced pressure at 120° C. to yeild 133 g of brown fluid.

Evaluation of Products

The product of the examples were evaluated using the Catalytic Oxidation Test as shown in Tables 1 and 2 below. The results demonstrate the remarkable antioxidant features of the examples with respect to control of the increase in viscosity and acidity. The Catalytic Oxidation Test may be summarized as follows: Basically the lubricant is subjected to a stream of air which is bubbled through the oil formulation at the rate of 5 liters per hour at 325° F. for 72 hours (Table 1) and 40 hours (Table 2) respectively. Present in the composition are samples of metals commonly used in engine construcion, namely iron, copper, aluminum and lead, see U.S. Pat. No. 3,682,980 incorporated herein by reference for further details.

TABLE 1

| | Catalytic Oxidation Test 325° F., 72 Hours | |
|---|---|---|
| Item | Change in Acid Number Δ TAN | Percent Change in Kinematic Viscosity Δ KV % |
| Base oil (100% solvent paraffinic neutral mineral oil) | 8.16 | 110.0 |
| 1% of Example 1 | 5.25 | 22.2 |
| 1% of Example 2 | 5.91 | 31.5 |

TABLE 2

| | Catalytic Oxidation Test 325° F., 40 Hours | |
|---|---|---|
| Item | Change in Acid Number Δ TAN | Percent Change in Kinematic Viscosity Δ KV % |
| Base oil (100% solvent paraffinic neutral mineral oil) | 6.63 | 66.3 |
| 1% of Example 1 | 0.47 | 4.6 |
| 1% of Example 2 | 0.74 | 6.6 |

The examples were also evaluated in accordance with standard corrosion test, ASTM-D 130-80 for copper strip corrosion at 250° F. for three hours. Both samples gave a rating of 1A which means substantially no corrosion for the test.

The antiwear properties of the examples were also evaluated using the Four Ball Wear Test data as shown in Table 3. The results clearly exhibit the good antiwear properties inherent in these unuiqe compositions.

In the Four Ball Wear Test three stationary balls are placed in a lubricant cup and a lubricant containing the compound to be tested is added thereto, and a fourth ball is placed in a chuck mounted on a device which can be used to spin the ball at known speeds and loads. The examples were tested using half inch stainless steel balls of 5 to 100 steel for 30 minutes under a 60 Kg load at 2000 rpms and 200° F. If additional information is desired consult test method ASTM D2266 and/or U.S. Pat. No. 4,761,482.

TABLE 3

| Four-Ball Wear Test | |
|---|---|
| Item | Wear Scar Diameter in mm, 30 minute test, 60 Kg load, 2000 RPM at 200° F. |
| Base oil (80% solvent paraffinic bright, 20% solvent paraffinic neutral mineral oils) | 3.78 |

TABLE 3-continued

| Four-Ball Wear Test | |
|---|---|
| Item | Wear Scar Diameter in mm, 30 minute test, 60 Kg load, 2000 RPM at 200° F. |
| 1% of Example 1 | 1.82 |
| 1% of Example 2 | 1.62 |

The data clearly illustrate (a) the method of providing "time release" antiwear property by blending appropriate sulfonate and cyclic phosphite components, and (b) use of the unique additive composition made by esterification of partially neutralized sulfonate with cyclic phosphites for use in lubricants and greases.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A product of reaction obtained by reacting a partially acidified hydrocarbyl sulfonate having from about 12 to about 32 carbon atoms with a phosphite derived from a diol or an amine, and having from about 10 to about 30 carbon atoms, the reaction being carried out at from about 50° C. to about 225° C. using a mole ratio of sulfonate to phosphite of from about 10:1 to about 1:10.

2. The product of claim 1 wherein the hydrocarbyl sulfonate is of the general formula:

$(ArSO_3)_n M$ where n is an integer equal to the valence number of M, M is (1) alkali metal or alkaline earth metal, (2) a nitrogenous group or a mixture of (1) and (2) and Ar is a $C_{12}$ to about a $C_{32}$ dialkylnaphthalene, dihydrocarbylarene or alkylaromatic group.

3. The product of claim 2 wherein M is an alkaline earth metal.

4. The product of claim 3 wherein M is selected from calcium or barium, or magnesium.

5. The product of claim 4 wherein M is calcium.

6. The product of claim 5 wherein the hydrocarbyl sulfonate is calcium dinonylnaphthalene sulfonate.

7. The product of claim 1 wherein the amine derived phosphite is prepared from amines selected from the group consisting of alkoxylated amines, alkoxylated hydrocarbyl amines, alkoxylated hydrocarbyl diamines, alkoxylated ether amines and mixtures thereof.

8. The product of claim 1 wherein the amine phosphite is made by reacting an alkoxylated amine of the formula:

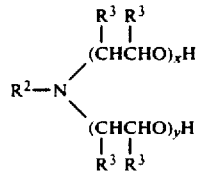

wherein $R^2$ is a $C_6$ to about $C_{30}$ hydrocarbyl group or a $C_6$ to about $C_{30}$ sulfur, nitrogen or oxygen-containing hydrocarbyl group or a mixture thereof, $R^3$ is hydrogen or a $C_1$ to $C_6$ hydrocarbyl group, and x and y are integers of from 0 to 50, at least one of which is not 0, with a phosphite of the formula:

$$(R^4O)_2\overset{\overset{\displaystyle O}{\|}}{P}-R^5$$

wherein $R^4$ is a $C_1$ to $C_6$ hydrocarbyl group and $R^5$ is hydrogen or a $C_1$ to $C_6$ hydrocarbyl group.

9. The product of claim 8 wherein $R^2$ is a $C_6$ to $C_{30}$ hydrocarbyl group selected from alkyl, aryl, alkenyl, alkaryl, aralkyl or cycloalkyl.

10. The product of claim 8 wherein said alkoxylated amine is bis(2-hydroxyethyl)-oleylamine.

11. The product of claim 1 wherein the diol derived phosphite is prepared from (1) a dihydrocarbyl or functionalized phosphite having the general formula:

$$(RO)_2\overset{\overset{\displaystyle O}{\|}}{P}-H$$

where each R is the same or different and is a hydrocarbyl group containing from 1 to about 20 carbon atoms and (2) a hydrocarbyl or functionalized diol having the generalized formula:

$$R^1(OH)_2$$

where $R^1$ is a hydrocarbyl group containing from 10 to about 30 carbon atoms or a hydrocarbyl group containing from 10 to about 30 carbon atoms and sulfur, nitrogen, oxygen or mixtures thereof.

12. The product of claim 11 wherein R is selected from the group consisting of methyl, ethyl, propyl, butyl, pentyl, hexyl and mixtures thereof.

13. The product of claim 11 wherein the diol is selected from the group consisting of 1,2-decanediol, 1,2-dodecanediol, 1,2-tetradecanediol, 1,2-pentadecanediol, 1,2-hexadecanediol, 1,2-heptadecanediol, 1,2-octadecanediol or diol esters or mixtures thereof.

14. The product of claim 13 wherein the diol esters are selected from glycerol monooleate, trimethylolpropanemonooleate, trimethylolpropane monostearate, trimethylolpropane monohexanate, glcycerol monohexanoate; pentaerythritol didecanoate and pentaerythritol diisosterate.

15. The product of claim 11 wherein said phosphite is a cyclic phosphite.

16. The product of claim 1 wherein the hydrocarbyl sulfonate is calcium dinonylnaphthalene sulfonate and the phosphite is a mixed hexadecane-octadecane-1,2-diol phosphite.

17. The product of claim 1 wherein the hydrocarbyl sulfonate is calcium dinonylnaphthalene sulfonate and the phosphite is the reaction product of tributyl phosphite and bis(2-hydroxyethyl)oleylamine.

18. A lubricant composition comprising a major proportion of lubricating oil or grease or other solid lubricant prepared therefrom and a minor multifunctional antioxidant, friction reducing, anitcorrosion amount of a product of reaction obtained by reacting a partially acidified hydrocarbyl sulfonate having from about 12 to about 32 carbon atoms with a diol-derived phosphite or an amine-derived phosphite having from about 10 to about 30 carbon atoms, the reaction being carried out at from about 50° C. to about 225° C. using a mole ratio of sulfonate to diol or amine phosphite of from about 10:1 to about 1:10.

19. The composition of claim 18 wherein the hydrocarbyl sulfonate is of the general formula:

$$(ArSO_3)_nM$$

wherein n is an integer equal to the valence number of M, M is alkali metal or alkaline earth metal or a nitrogenous group or mixtures thereof and Ar is a $C_{12}$ is about a $C_{32}$ dialkylnaphthalene, dihydrocabylarene or alkylaromatic group.

20. The composition of claim 19 wherein M is an alkaline earth metal.

21. The composition of claim 20 wherein M is calcium.

22. The composition of claim 21 wherein the hydrocarbyl sulfonate is calcium dinonylnaphthalene sulfonate.

23. The composition of claim 18 wherein the amine phosphite is prepared from amines selected from the group consisting of alkoxylated amines, alkoxylated hydrocarbyl amines, alkoxylated hydrocarbyl diamines, or alkoxylated ether amines and mixtures thereof.

24. The composition of claim 18 wherein the diol-derived phosphite has the following generalized formula $$(RO)_2\overset{\overset{\displaystyle O}{\|}}{P}-H$$

where each R is the same or different and is a hydrocarbyl group containing from 1 to about 20 carbon atoms, and the diol is a hydrocarbyl or functionalized diol having the generalized formula:

$$R^1(OH)_2$$

where $R^1$ is a hydrocarbyl group containing from 10 to about 30 carbon atoms or a hydrocarbyl group containing from 10 to about 30 carbon atoms and sulfur, nitrogen or oxygen or mixtures thereof.

25. The composition of claim 24 wherein R is selected from the group consisting of methyl, ethyl, propyl, butyl, pentyl, hexyl and mixtures thereof.

26. The composition of claim 24 wherein the diol is selected from the groups consisting of 1,2-decanediol, 1,2-dodecanediol, 1,2-tetradecanediol, 1,2-pentadecanediol, 1,2-hexadecanediol, 1,2-heptadecanediol, 1,2-octadecanediol or diol esters or mixtures thereof.

27. The composition of claim 26 wherein the diol esters are selected from glycerol monooleate, trimethylolpropane monostearate, trimethylolpropane monohexanate, trimethylolpropane monooleate, gylcerol monohexanoate, pentaerythritol didecanoate, and pentaerythritol diisosterate.

28. The composition of claim 23 made by reacting an alkoxylated amine of the formula:

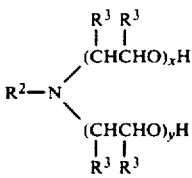

wherein $R^2$ is a $C_6$ to $C_{30}$ hydrocarbyl group or a $C_6$ to about $C_{30}$ sulfur, nitrogen or oxygen-containing hydrocarbyl group or a mixture thereof, $R^3$ is hydrogen or a $C_1$ to $C_6$ hydrocarbyl group, and x and y are intergers of from 0 to 50, at least one of which is not 0, and a phosphite is of the formula:

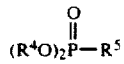

wherein $R^4$ is a $C_1$ to $C_6$ hydrocarbyl group and $R^5$ is hydrogen or $C_1$ to $C_6$ hydrocarbyl.

29. The composition of claim 28 wherein $R^2$ is $C_6$ to $C_{30}$ hydrocarbyl and is selected from alkyl, aryl, alkenyl, alkaryl, aralkyl or cycloalkyl.

30. The composition of claim 28 wherein said alkoxylated amine is bis(2-hydroxyethyl)oleylamine.

31. The composition of claim 18 wherein the hydrocarbyl sulfonate is calcium dinonylnaphthalene sulfonate and the amine-phosphite is the reaction product of tributylphosphite and bis(2-hydroxyethyl)oleylamine.

32. The composition of claim 18 wherein the hydrocarbyl sulfonate is calcium dinonylnaphthalene sulfonate and the phosphite is mixed hexadecane-octadecane-1,2-diol phosphite.

33. The composition of claim 18 wherein the lubricant is selected from the group consisting of (1) mineral oils (2) synthetic oils or mixture of synthetic oils, (3) a mixture of (1) and (2), and (4) a grease prepared from any one of (1), (2) or (3).

34. The composition of claim 33 wherein the lubricant is a mineral oil.

35. The composition of claim 33 wherein the lubricant is a synthetic oil.

36. The composition of claim 33 wherein the lubricant is a mixture of oils defined by (3).

37. The composition of claim 33 wherein the lubricant is a grease or other solid lubricant prepared from any one of (1), (2) or (3).

38. A method of reducing fuel consumption in an internal combustion engine comprising contacting and lubricating the moving parts of said engine with a composition comprising a major proportion of a lubricating oil and a fuel reducing/multifunctional additive amount of a product of reaction obtained by reacting a partially acidified hydrocarbyl sulfonate with a diol phosphite or amine-phosphite having from about 10 to about 30 carbon atoms, the reaction being carried out at from about 50° C. to about 225° C. using a mole ratio of sulfonate to diol or amine-phosphite of from about 10:1 to about 1:10.

39. A method of providing timed release multifunctional friction reducing, antioxidant, antiwear and anticorrosion characteristics to lubricant compositions comprising (1) blending into a major amount of said lubricant composition a minor amount of hydrocarbyl sulfonate and diol-or amine-derived hydrocarbyl phosphite, in a mole ratio of sulfonate to phosphite of from about 10:1 to 1:10, (2) at least partially acidifying the sulfonate in situ or in service and thereafter (3) co-reacting the acidified sulfonate and said phosphite while said lubricant is in use.

40. The method of claim 39 wherein said reaction takes place at temperatures varying from ambient or about 50° C. to about 225° C., at ambient pressures in a lubricant composition comprising a major amount of an oil of lubricating viscosity or grease or other solid lubricant prepared therefrom.

41. The method of claim 39 wherein the hydrocarbyl phosphite contains from 10 to about 30 carbon atoms and the hydrocarbyl sulfonate contains from 12 to about 32 carbon atoms.

42. The method of claim 39 wherein the hydrocarbyl sulfonate is partially acidified as generally described below:

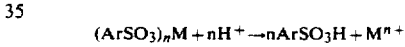

where n is an integer equal to the valence number of M, M is alkali metal, alkaline earth metal or a nitrogenous group or mixture thereof and Ar is a $C_{12}$ to about a $C_{32}$ dialkylnaphthalene, dihydrocarbylarene or alkylaromatic group.

* * * * *